United States Patent [19]
Vrieland et al.

[11] 4,322,538
[45] Mar. 30, 1982

[54] PREPARATION OF SYMMETRICAL TETRACHLOROPYRIDINE

[75] Inventors: Gail E. Vrieland, Midland, Mich.; Bart J. Bremmer, Ashland, Mass.; Richard E. Crooks, Bay City, Mich.

[73] Assignee: The Dow Chemical Company, Midland, Mich.

[21] Appl. No.: 255,602

[22] Filed: Apr. 20, 1981

[51] Int. Cl.³ .......................................... C07D 213/02
[52] U.S. Cl. .................................................. 546/345
[58] Field of Search ........................................ 546/345

[56] References Cited
U.S. PATENT DOCUMENTS 3,420,833  1/1969  Taplin ................................. 546/180
3,538,100  11/1970  Smith ................................. 546/345
3,993,654  11/1976  Dean et al. ......................... 546/345

FOREIGN PATENT DOCUMENTS 539034  12/1976  U.S.S.R. .............................. 546/345

OTHER PUBLICATIONS

Collins et al., Journal of the Chemical Society (C), pp. 167-174, London, (1971).

Primary Examiner—Alan L. Rotman
Attorney, Agent, or Firm—John M. Sanders

[57] ABSTRACT

Symmetrical tetrachloropyridine (2,3,5,6-tetrachloropyridine) is prepared by reacting pentachloropyridine with a source of iodide ions in the presence of a proton source and a solvent medium. The reaction is preferably carried out in a polar, aprotic solvent medium and heated at a temperature of from about 100° C. to about 200° C.

10 Claims, No Drawings

PREPARATION OF SYMMETRICAL TETRACHLOROPYRIDINE

BACKGROUND OF THE INVENTION

1. Field of the Invention

This invention pertains to a new and improved process for preparing symmetrical tetrachloropyridine from pentachloropyridine. Tetrachloropyridine is an important commercial product which is used extensively in the preparation of insecticides.

2. Prior Art Description

Symmetrical tetrachloropyridine is prepared through a variety of processes. In a process as taught in Russian Pat. No. 539,034, an alkali dialkyl phosphite in N,N-dimethylformamide is added to 4-iodotetrachloropyridine, to form the desired symmetrical tetrachloropyridine. The reaction is carried out at temperatures from 140° C. to 160° C.

In U.S. Pat. No. 3,538,100, symmetrical tetrachloropyridine is prepared from the reaction of 2,6-dichloropyridine and chlorine in the presence of a catalyst. Pentachloropyridine is also produced as a contaminating by-product.

Another method for producing symmetrical tetrachloropyridine is by the reaction of pentachloropyridine with an oxidizable metal (e.g., Zn) in the presence of an acid (e.g., aqueous HCl). According to Dean et al. in U.S. Pat. No. 3,993,654, this reaction is run in an aqueous medium at a temperature of 110° C. However, due to the cost and corrosive nature of the reaction mixture, other methods of preparation are desirable.

SUMMARY OF THE INVENTION

The reaction of pentachloropyridine with a source of iodide ions and a proton donor in a solvent to form symmetrical tetrachloropyridine takes place in high yield and in a reasonable time period provided the reactants are heated sufficiently. The product is recovered by known techniques such as distillation.

DETAILED DESCRIPTION OF THE INVENTION

The present invention is a process for replacing the 4-chloro substituent in pentachloropyridine with hydrogen by reacting the pentachloropyridine with a source of iodide ions and a proton donor to form symmetrical tetrachloropyridine (2,3,5,6-tetrachloropyridine). Suitable sources of iodide ions are sodium iodide, and other solvent soluble metal iodide salts or ammonium iodide salts.

The reaction is normally conducted by blending pentachloropyridine with an iodide salt dissolved in a suitable solvent, all in the presence of a proton source such as water and/or sodium bicarbonate. Normally an organic solvent with a small amount of water serves as the reaction solvent and also as the proton source. Polar, aprotic solvents are appropriate organic solvents; examples are dimethylacetamide, methyl ethyl ketone, acetic acid, N,N-dimethylformamide, N-formylpiperidine, N-methylpyrrolidone, sulfolane and ethyl acetoacetate.

The reaction proceeds slowly at ambient room temperature and because of this, a temperature is normally chosen in the range of from about 100° C. to about 200° C. with the preferred temperatures ranging from about 130° C. to about 160° C.

While the reaction occurs with any ratio of reactants, it is advantageous that the limits of the solvent to pentachloropyridine weight ratio are about 1 to about 20. Preferred ratios are about 2 to about 5. The mole ratio of iodide ion to pentachloropyridine is usually about 0.1 to about 4. The preferred range is about 0.2 to about 2. A suitable solvent to iodide ion mole ratio is about 2 to 7. The mole ratio of the proton source to pentachloropyridine is advantageously from about 0.5 to about 4. The preferred range is about 0.5 to about 2.

When practicing the present invention at various aforementioned temperatures, mole ratios and weight ratios, a high product yield is achievable which is usually greater than about 80 percent of theoretical, based on the amount of pentachloropyridine employed as a starting material.

The reaction mixture is heated until iodine is formed and it is advantageous to reduce the iodine back to iodide for recycle rather than recovering it as elemental iodine. A reducing agent is, therefore, normally added to the reaction mixture to reduce the iodine as it is formed. Suitable examples of reducing agents are sodium formate, sodium sulfite, formic acid and sodium thiosulfate. In a preferred method of reduction, a combination of sodium sulfite, as the reducing agent, and sodium bicarbonate, as the proton donor, are employed. Both of these compounds may be added at the beginning of the reaction as solids. Another preferred method is to generate sodium formate in situ by pumping liquid formic acid into the basic reaction mixture rather than adding the sodium formate as a solid. When generating sodium formate in situ, by the addition of liquid formic acid, the formic acid functions as the proton donor.

At the completion of the reaction, the symmetrical tetrachloropyridine product is recovered by conventional techniques such as by distillation or other such methods.

The following examples further illustrate the invention but are not to be construed as limitations on the scope of the process contemplated herein.

EXAMPLE 1

Pentachloropyridine (PCP) (10 g) (0.046 mole), NaI (11.9 g) (0.079 mole), and $NaHCO_3$ (3.35 g) (0.04 mole) were dissolved in 23.42 g (0.269 mole) of N,N-dimethylacetamide (DMAC) and heated to 160° C. for 4 hours in a 125 cubic centimeter (cc) round bottom flask with stirring. A total of 2.5 g sodium formate was added in equal portions every half hour over the 4 hours. The reaction mixture was mixed with 100 cc of toluene and 100 cc of water and the toluene layer was analyzed against an internal standard (1,2,4-trichlorobenzene) by vapor phase chromatography. The analysis results indicated 96.1 percent conversion of PCP to tetrachloropyridine of which 89.8 percent was symmetrical tetrachloropyridine.

EXAMPLE 2

PCP (30.0 g) (0.138 mole), NaI (35.7 g) (0.238 mole), $NaHCO_3$ (10.2 g) (0.121 mole) and $Na_2SO_3$ (15.1 g) (0.120 mole) were dissolved in 70.25 g (0.807 mole) of DMAC and heated, with stirring, to 160° C. for approximately 5 hours. Using substantially the same recovery and analysis procedures employed in Example 1, the analysis results indicated the conversion of PCP to symmetrical tetrachloropyridine was 91.7 percent of theoretical.

EXAMPLE 3

PCP (20.0 g) (0.0922 mole), NaI (23.85 g) (0.159 mole), Na$_2$CO$_3$ (10.12 g) (0.080 mole), water (1.72 g) (0.096 mole) and Na$_2$SO$_3$ (15.06 g) (0.120 mole) were dissolved in DMAC (69.1 g) (0.794 mole) and heated to 160° C. for approximately 5 hours. Using substantially the same recovery and analysis procedures employed in Example 1, the analysis results indicated the conversion of PCP to symmetrical tetrachloropyridine was 92.0 percent of theoretical.

EXAMPLE 4

PCP (30 g) (0.138 mole), NaI (36.2 g) (0.241 mole), Na$_2$CO$_3$ (7.6 g) (0.072 mole) were added to DMAC (80.2 g) (0.922 mole) and this mixture was heated to about 150° C. After one hour liquid formic acid was pumped into the reaction mixture at a rate of 0.19 mole/mole of PCP/hour. After 3 hours the temperature was raised to 155° C. for 3 hours and then to 160° C. for 2 more hours at which time the formic acid addition was stopped. Using substantially the same recovery and analysis procedures employed in Example 1, the analysis results indicated the conversion of PCP to symmetrical tetrachloropyridine was 88.3% of theoretical.

Similar excellent high yield results are achieved when the procedures employed in the foregoing examples are repeated using various different amounts of solvent, PCP, proton source and iodide ion within the scope of the weight and mole ratios described herein.

What is claimed is:

1. A process for preparing 2,3,5,6-tetrachloropyridine comprising
   (a) admixing pentachloropyridine, iodide ions and a proton donor in a polar, aprotic solvent to form a reaction mixture and
   (b) heating said reaction mixture to a temperature in the range of from about 100° C. to about 200° C. until 2,3,5,6-tetrachloropyridine is formed in a high yield.

2. The process defined by claim 1, wherein said polar, aprotic solvent is dimethylacetamide, methyl ethyl ketone, acetic acid, N,N-dimethylformamide, N-formylpiperidine, N-methylpyrolidone, sulfolane, ethyl acetoacetate or a mixture thereof.

3. The process defined by claim 1, wherein the weight ratio of polar aprotic solvent to pentachloropyridine is about 1 to about 20, the mole ratio of iodide ion to pentachloropyridine is about 0.1 to about 4, the mole ratio of polar aprotic solvent to iodide is about 2 to about 7, and the mole ratio of the proton source to pentachloropyridine is about 0.5 to about 4.

4. The process defined by claim 1, wherein said process is carried out in the presence of a reducing agent.

5. The process defined by claim 4, wherein said reducing agent is sodium formate, sodium sulfite, formic acid, or sodium thiosulfate.

6. The process defined by claim 4, wherein said iodide ions are derived from sodium iodide, said proton donor is sodium bicarbonate and said reducing agent is sodium sulfite and said reaction mixture is dissolved in dimethylacetamide and heated to a temperature of from about 130° C. to about 160° C.

7. The process defined by claim 1, wherein said proton donor is sodium bicarbonate.

8. The process defined by claim 1 wherein said proton donor is sodium carbonate and water.

9. The process defined by claim 1, wherein said iodide ions are derived from sodium iodide.

10. The process defined by claim 1, wherein said reaction mixture is heated to a temperature of from about 130° C. to about 160° C.

* * * * *